United States Patent
Borowy-Borowski et al.

[19]

[11] Patent Number: 6,045,826
[45] Date of Patent: Apr. 4, 2000

[54] WATER-SOLUBLE COMPOSITIONS OF BIOACTIVE LIPOPHILIC COMPOUNDS

[75] Inventors: Henryk Borowy-Borowski, Glouester; Marianna Sikorska-Walker; P. Roy Walker, both of Navan, all of Canada

[73] Assignee: National Research Council of Canada, Ottawa, Canada

[21] Appl. No.: 09/285,244

[22] Filed: Apr. 2, 1999

[51] Int. Cl.$^7$ ................................. A61K 9/48; A61K 9/14
[52] U.S. Cl. .................... 424/451; 424/452; 424/464; 424/465; 424/486; 424/489; 424/502; 514/458; 514/772.3; 514/960
[58] Field of Search ..................... 424/451, 464, 424/465, 489, 502, 452, 486; 514/458, 960, 772.3

[56] References Cited

U.S. PATENT DOCUMENTS

| | | |
|---|---|---|
| 2,680,749 | 6/1954 | Cawley et al. |
| 4,189,400 | 2/1980 | Proksch et al. |
| 4,224,229 | 9/1980 | Proksch et al. |
| 5,179,122 | 1/1993 | Greene et al. |
| 5,234,695 | 8/1993 | Hobbs et al. |
| 5,558,876 | 9/1996 | Desai et al. |
| 5,593,105 | 1/1997 | Schmid et al. |
| 5,593,682 | 1/1997 | Papas et al. |
| 5,686,110 | 11/1997 | Greenwald et al. |
| 5,798,333 | 8/1998 | Sherman. |
| 5,891,469 | 4/1999 | Amselem. |

FOREIGN PATENT DOCUMENTS

96/17626   6/1996   WIPO.

*Primary Examiner*—Thurman K. Page
*Assistant Examiner*—Brian K. Seidlech
*Attorney, Agent, or Firm*—J. Wayne Anderson

[57] ABSTRACT

Water-soluble compositions comprising a lipophilic compound and a solubilizing agent of the general formula:

$$\{X-OOC-[(CH_2)_n-COO]_m\}_p-Y \quad (I)$$

wherein:
X is a residue of a hydrophobic moiety,
Y is a residue of a hydrophilic moiety,
p is 1 or 2,
m is 0 or 1, and
n is an integer greater than or equal to 0 are disclosed. The lipophilic compound is preferably selected from the group consisting of water-insoluble ubiquinones, ubiquinols, vitamins, provitamins, polyene macrolide antibiotics, and mixtures thereof. The hydrophobic moiety is preferably a sterol or a tocopherol and the hydrophilic moiety is preferably a polyalkylene glycol. In preferred embodiments, the sterol is cholesterol or sitosterol, the tocopherol is a-(+)-tocopherol, the polyalkylene glycol is a polyethylene glycol or its methyl monoether having an average molecular weight between 600 and 1000, p is equal to 1 or 2, m is equal to 0 or 1 and n is an integer between 2 and 18.

45 Claims, 5 Drawing Sheets

Figure 3. The effect of PTS - $CoQ_{10}$ composition on cellular ATP level in NT2 cells
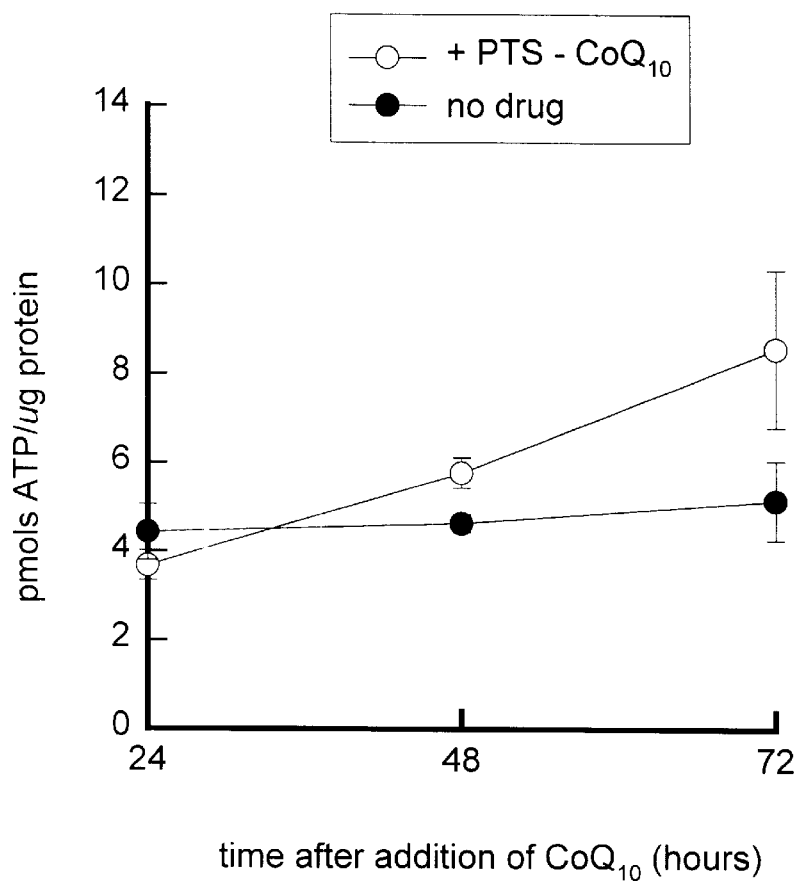

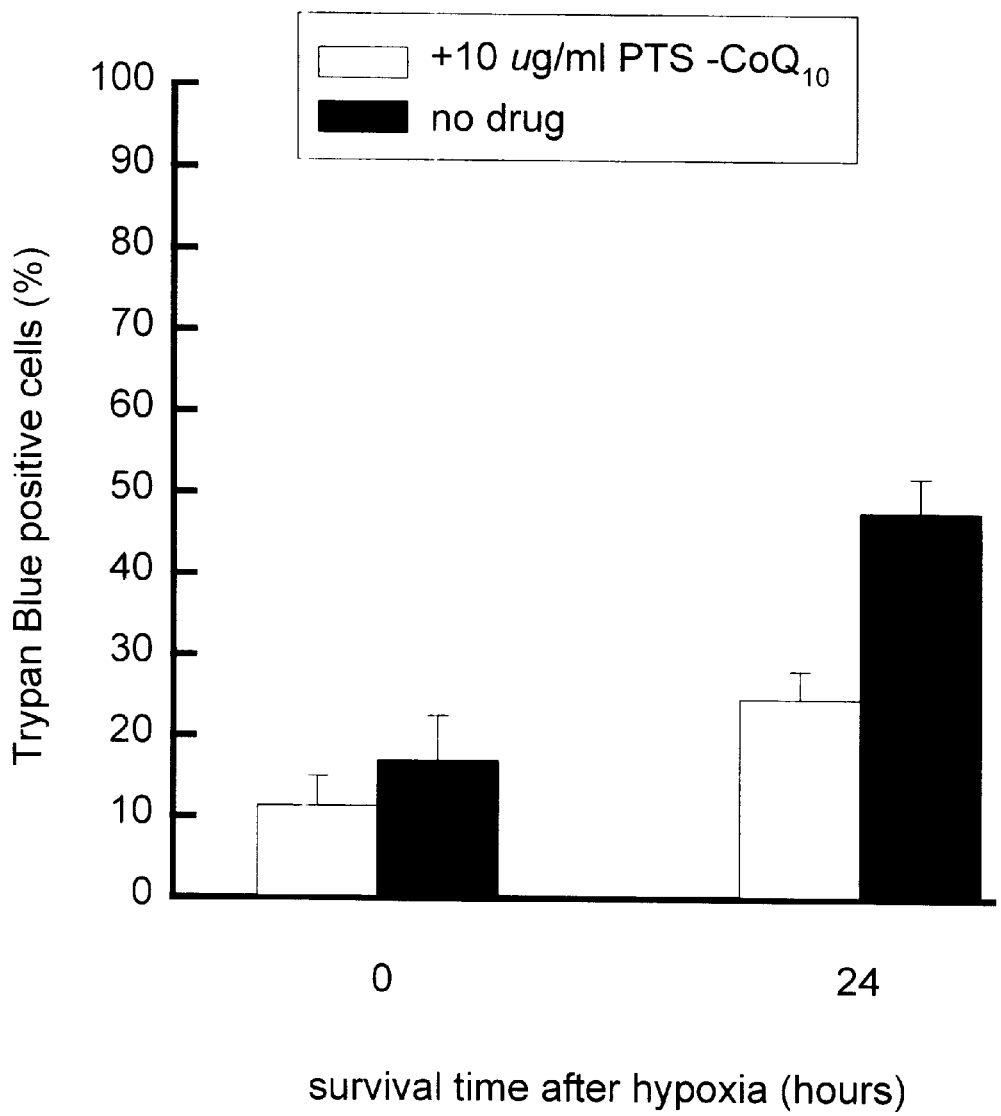
Figure 4. Protective effect of PTS-CoQ$_{10}$ formulation against hypoxia in NT2 cells

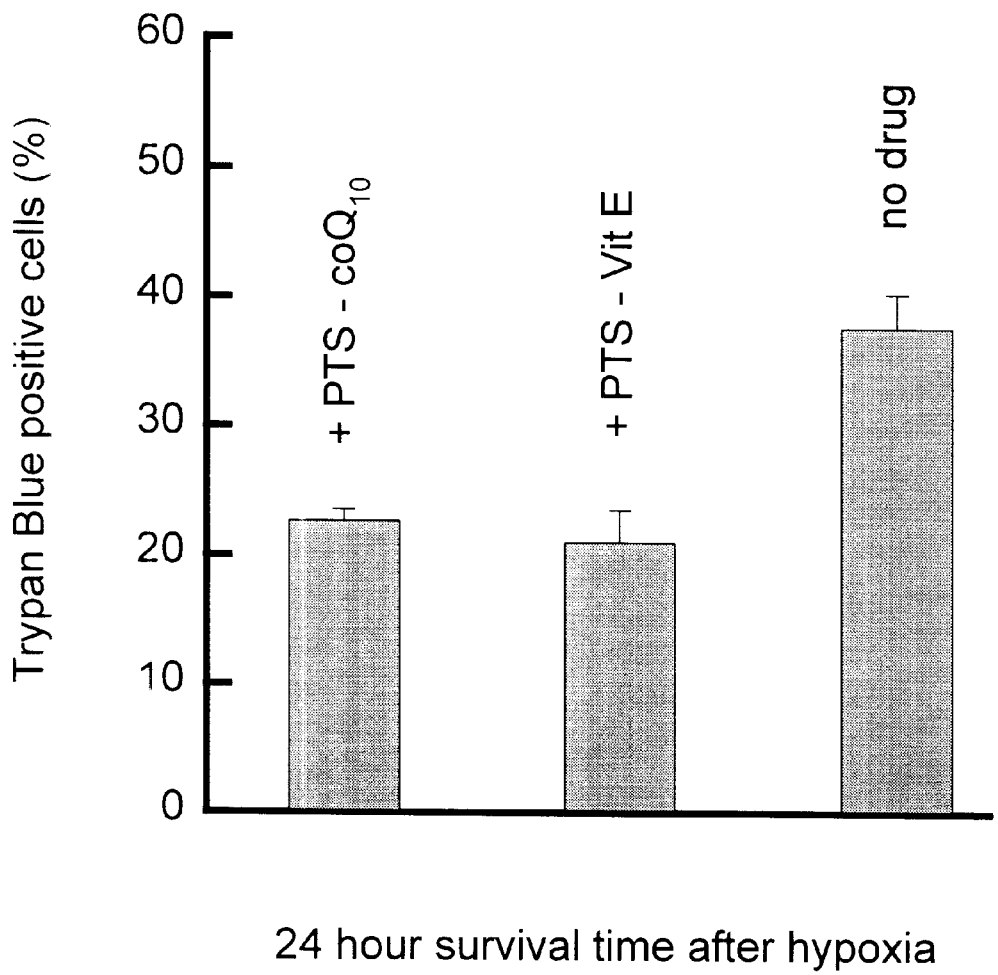
Figure 5. The effects of PTS - $coQ_{10}$ and PTS - Vit E on the viability of hypoxia treated NT2 cells

WATER-SOLUBLE COMPOSITIONS OF BIOACTIVE LIPOPHILIC COMPOUNDS

FIELD OF THE INVENTION

The present invention relates to water-soluble compositions of bioactive lipophilic compounds, to compounds useful for the preparation of such compositions, to methods of preparing such compounds and compositions, and to the use of such compositions as therapeutics and cosmetics.

BACKGROUND OF THE INVENTION

Many bioactive compounds are highly lipophilic (hydrophobic), meaning that they are soluble in lipids (oils) and some organic solvents, while being substantially insoluble or only sparsely soluble in water. The lack of solubility of a bioactive compound in aqueous media is an important factor limiting its therapeutic applications, making difficult an efficient administration of the compound to a patient. When administered in the form of an oil solution or some kind of water and/or oil suspension or emulsion, lipophilic compounds usually show a poor bioavailability, meaning a low concentration and a long build-up time of the compound in the systemic circulation. This lack of bioavailability is usually independent of the administration route (topical, oral, or parenteral).

Various approaches to overcoming this limitation are known in the prior art. One known approach consists of dissolving a lipophilic compound in a water-miscible organic solvent, such as ethanol or propylene glycol. When such a solution is admixed with blood or gastrointestinal fluids, however, the lipophilic compound usually precipitates as a solid or liquid emulsion, with a resulting low bioavailability. Furthermore, for many lipophilic compounds no organic, water-miscible solvents exist. Another approach consists of incorporating lipophilic compounds into various compositions, frequently inhomogeneous, multiphase emulsions, containing oils and solvents in combination with surfactants. These compositions may improve the bioavailability of the compound without significantly increasing its solubility in aqueous media, but are normally suitable only for a particular administration form, usually for topical applications. Such compositions, which may also induce a protective immune response in mammals, are of little value for therapeutic uses where administration of the compound by ingestion or injection is necessary and where an aqueous solution or a water-soluble solid composition is frequently the only acceptable administration form.

Several approaches to preparing homogenous aqueous solutions of lipophilic bioactive compounds are also known in the prior art. One method consists of preparing a derivative or an analog of a lipophilic compound having a better solubility in water than the original compound. In the simplest case, this derivative may be a water-soluble salt of the compound, which salt usually retains the original biological activity, but this approach is applicable only to compounds having acidic or basic properties. If more substantial modifications are introduced into the original compound to improve its solubility, a decrease or even a complete loss of the original bioactivity of the compound is frequently observed.

Another method of solubilization consists of preparing a water-soluble derivative capable of liberating the original bioactive compound under physiological conditions. Such derivatives, also known as pro-drugs, usually improve bioavailability of the compound and may also ensure a targeted delivery of the compound or its sustained release over a period of time. However, this approach usually relies on the presence of certain functional groups in the original compound, so it is not universally applicable. In addition, synthetic methods of improving solubility of a compound by chemical modifications are relatively complicated and expensive.

Still another approach to solubilization of bioactive lipophilic compounds relies on formation of water-soluble complexes. An example are complexes with amphipathic compounds containing moieties of two opposing solubility tendencies (lipophilic and hydrophilic). Such compounds are often soluble both in organic solvents and in water, so that the solubilization is usually achieved by dissolving a bioactive lipophilic compound and an amphipathic compound in a suitable water-miscible organic solvent and diluting the solution with water. In some cases the organic solvent is partially or entirely removed from the original or water-diluted solution by evaporation or lyophilization and the concentrate reconstituted with a suitable aqueous medium, without precipitation of the water-insoluble lipophilic compound. When the auxiliary organic solvent cannot be completely removed from the composition, this solvent must be pharmaceutically acceptable, which limits the choice of applicable solvents.

Bioactive lipophilic compounds in need of solubilization belong to various therapeutic categories, such as vitamins (e.g., Vitamin E), antibiotics, in particular macrolide polyene antibiotics (amphotericin-B, nystatin, candicidin), free radicals scavengers (e.g., tocopherols, ubiquinones), immunosuppressants (e.g., cyclosporine), etc. Various approaches to achieve the solubility and improve the bioavailability of these and other lipophilic compounds are known in the prior art, including formation of water-soluble complexes.

U.S. Pat. No. 5,686,110 discloses water-soluble complexes of water-insoluble compounds, including amphotericin-B and cyclosporine, with a polyalkylene oxide polymers end-capped with an alkyl or olefinic group, which polymers are soluble both in water and in organic solvents. The water-soluble complexes, which are formed only in the presence of an auxiliary organic solvent, are lyophilized and reconstituted with a buffer solution. The reconstituted aqueous solutions show only a limited stability, depending mostly on the pH of the solution. Furthermore, the use of methoxypolyethylene glycol polymers of relatively high molecular weight (2,000 to 5,000) as preferred solubilizing agents increases the amount by weight of polymer necessary for solubilization of the bioactive compound.

U.S. Pat. No 5,798,333 discloses a homogenous, water-soluble composition (concentrate) of cyclosporine, which can be diluted with an aqueous solution without precipitation of cyclosporine. The concentrate comprises cyclosporine and tocophersolan (polyoxyethanyl-a-tocopheryl succinate, TPGS) dissolved in a hydrophilic organic solvent, such as propylene glycol. Solvent-free compositions are not disclosed, as they would likely be unstable or in homogeneous.

WO 96/17626 discloses water-soluble compositions of ubiquinones comprising polyoxyethanyl-cholesteryl sebacate (PCS) as a solubilizing agent. A ubiquinone, in particular Coenzyme $Q_{10}$, is solubilized by dissolving both Coenzyme $Q_{10}$ and PCS in tetrahydrofuran at an approximate molar ratio of 1:3 and diluting this solution with water. The solution is then evaporated to dryness under reduced pressure and reconstituted with a suitable buffer solution.

Coenzyme $Q_{10}$ (CoQ10) is a natural compound whose therapeutic potential has been recently recognized for a number of disorders, including congestive heart failure, muscular distrophy, periodontal disease, correction of drug-induced deficiencies, and immune restoration (AIDS, allergies), to name a few. Coenzyme $Q_{10}$ is also of great interest to cosmetic industry, since it can be included into cosmetic preparations as agent slowing down natural skin ageing processes. The biological activity of Coenzyme $Q_{10}$ is believed to be linked to its ability to act as an antioxidant and free radical scavenger protecting integrity of cell membranes and to offset the inability of diseased cells to manufacture sufficient energy for cellular repair, by stimulating mitochondrial respiration and production of ATP. For effectiveness in both clinical and cosmetic applications, preparations of Coenzyme $Q_{10}$ with high bioavailability and solubility in aqueous media are usually required.

Even though various methods of improving solubility of lipophilic compounds, such as Coenzyme $Q_{10}$, in aqueous media are known in the prior art, they are not equal in terms of simplicity, scope of applicability, stability of the prepared formulations, etc. The present invention provides a new method of solubilization of lipophilic compounds, which is free of many prior art drawbacks and limitations.

SUMMARY OF THE INVENTION

According to one aspect, the present invention provides a water-soluble composition comprising a lipophilic compound and a solubilizing agent of the general formula:

$$\{X-OOC-[(CH_2)_n-COO]_m\}-Y \qquad (I)$$

wherein:
X is a residue of a hydrophobic moiety,
Y is a residue of a hydrophilic moiety,
p is 1 or 2,
m is 0 or 1, and
n is an integer greater than or equal to 0.

The lipophilic compound is preferably selected from the group consisting of ubiquinones, ubiquinols, vitamins, provitamins, polyene macrolide antibiotics, and mixtures thereof. The hydrophobic moiety is preferably a sterol or a tocopherol and the hydrophilic moiety is preferably a polyalkylene glycol. In preferred embodiments, the sterol is cholesterol or sitosterol, the tocopherol is a-(+)-tocopherol, the polyalkylene glycol is a polyethylene glycol or its methyl monoether having an average molecular weight between 600 and 1000, p is equal to 1 or 2, m is equal to 0 or 1 and n is an integer between 2 and 18.

According to another aspect, the invention provides a method of preparation and purification of a water-soluble composition comprising a solubilizing agent of the general formula (I), in the presence or in the absence of an auxiliary organic solvent. The solubilization is achieved by dissolving a water-insoluble lipophilic compound and a solubilizing agent in a water-miscible organic solvent, diluting the solution with water, and removing the organic solvent and optionally a part of water under reduced pressure. Alternatively, a lipophilic compound and solubilizing agent can be admixed directly in a predetermined molar ratio and heated to a temperature higher than the their respective melting points, to form a water-soluble composition in the form of a clear melt, which can be then diluted with an aqueous solution to a desired concentration. The water-soluble composition may be additionally purified by dissolving it in a small amount of water, heating the solution until the composition separates as a clear liquid phase, and removing the separated composition from the solution while keeping the temperature of the solution substantially unchanged.

According to still another aspect, the invention provides pharmaceutical or cosmetic formulations comprising a water-soluble composition of a lipophilic compound and a solubilizing agent of formula (I).

According to yet another aspect, the invention provides novel solubilizing agents of formula (I) and methods of their preparation and purification.

BRIEF DESCRIPTION OF THE DRAWINGS

FIG. 3 is a graph showing the effect of $PTS-CoQ_{10}$ composition on cellular ATP level in NT2 cells.

FIG. 4 is a graph showing the protective effect of $PTS-CoQ_{10}$ composition against hypoxia in NT2 cells.

FIG. 5 is a graph showing the effect of $PTS-CoQ_{10}$ and PTS-Vitamin E compositions on the viability of hypoxia-treated NT2 cells.

DETAILED DESCRIPTION OF THE PREFERRED EMBODIMENTS

Figure 1:
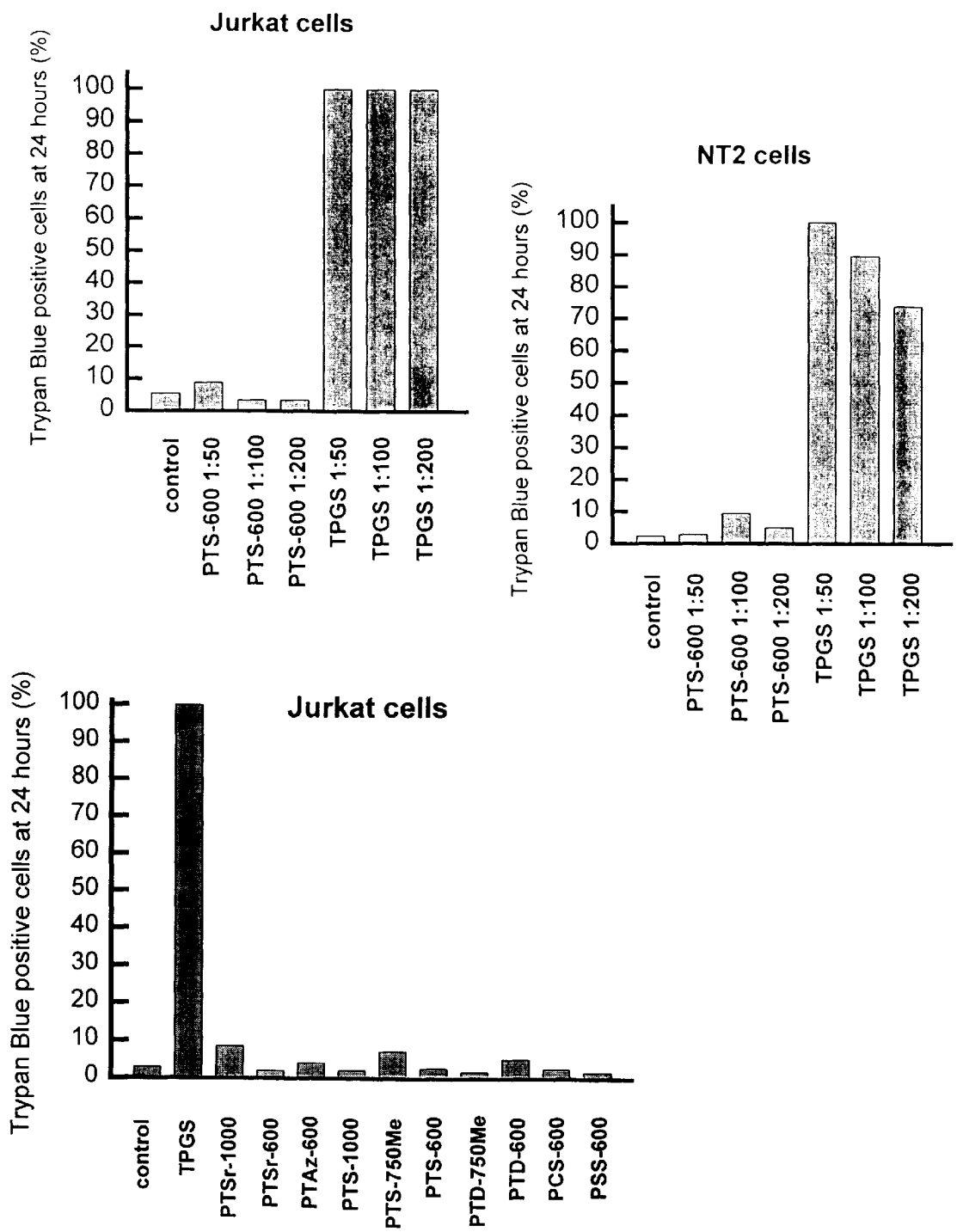
FIG. 1 is a graph showing the toxicity of various solubilizing agents.

The invention provides a method of solubilization of substantially water-insoluble, bioactive lipophilic compounds, by providing a water-soluble composition comprising the lipophilic compound and a solubilizing agent of the following general formula:

$$\{X-OOC-[(CH_2)_n-COO]_m\}_p-Y \qquad (I)$$

wherein:
X is a residue of a hydrophobic moiety,
Y is a residue of a hydrophilic moiety,
p is 1 or 2,
m is 0 or 1, and
n is an integer greater than or equal to 0.

The hydrophobic moiety of the solubilizing agent is a hydrophobic (lipophilic) molecule having an esterifiable hydroxy group and is preferably a sterol or a tocopherol, in particular cholesterol, 7-dehydrocholesterol, campesterol, sitosterol, ergosterol, stigmasterol, or an a-, b-, g-, or d-tocopherol. Cholesterol and sitosterol are preferred sterols, sitosterol being particularly preferred. a-(+)-Tocopherol and a-(±)-tocopherol are preferred tocopherols, a-(+)-tocopherol (vitamin E) being particularly preferred. The residue of the hydrophobic moiety is the entire hydrophobic molecule, except for its esterified hydroxy group, such as 3-b-hydroxy group of cholesterol or sitosterol or 6-hydroxy group of a-tocopherol.

The hydrophilic moiety of the solubilizing agent is a hydrophilic molecule having an esterifiable hydroxy or carboxy group, and is preferably selected from the group consisting of polyalcohols, polyethers, polyanions, polycations, polyphosphoric acids, polyamines, polysaccharides, polyhydroxy compounds, polylysines, and derivatives thereof. Of those, polyethers are preferred, polyalkylene glycols being particularly preferred. The term "polyalkylene glycol" includes polymers of lower alkylene oxides, in particular polymers of ethylene oxide (polyethylene glycols) and propylene oxide (polypropylene glycols), having an esterifiable hydroxy group at least at one end of the polymer molecule, as well as derivatives of such polymers having esterifiable carboxy groups. The residue of the hydrophilic moiety is the entire hydrophilic molecule, except for its esterified hydroxy or carboxy group or groups, such as terminal hydroxy groups of a polyethylene glycol molecule.

Polyethylene glycols are most particularly preferred for the practice of the present invention. Suitable polyethylene glycols may have a free hydroxy group at each end of the polymer molecule, or may have one hydroxy group etherified with a lower alkyl, e.g., a methyl group. Also suitable for the practice of the invention are derivatives of polyethylene glycols having esterifiable carboxy groups. Polyethylene glycols are commercially available under the trade name PEG, usually as mixtures of polymers characterized by an average molecular weight. Polyethylene glycols having an average molecular weight from about 300 to about 5000 are preferred, those having an average molecular weight from about 600 to about 1000 being particularly preferred.

Compounds of formula (I) for which m is equal to 1 can be regarded as diesters of an alkanedioic acid of the general formula HOOC—$(CH_2)_n$—COOH. For the practice of the present invention, alkanedioic acids with n from 0 to 18 are preferred, those with n from 6 to 10 being particularly preferred. Sebacic acid (n=8) is most particularly preferred.

Bioactive lipophilic compounds which can be solubilized using solubilizing agents of the present invention belong to a variety of therapeutic and chemical categories and include ubiquinones, ubiquinols, sterols, vitamins, provitamins and macrolide polyene antibiotics.

Preferred ubiquiniones and ubiquinols are those of the formula:

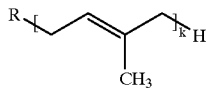

wherein R is

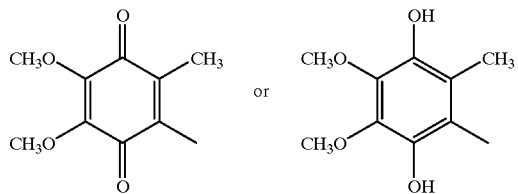

and k is an integer of from 6 to 12. Those with k equal to 10 (ubiquinone-50 or Coenzyme $Q_{10}$ and ubiquinol-50 or reduced Coenzyme $Q_{10}$, respectively) are particularly preferred.

Cholesterol, sitosterol, ergosterol and 7-dehydrocholesterol are preferred sterols. Vitamins A, D, E, and K are preferred vitamins and provitamin A (b-carotene) is a preferred provitamin. Amongst macrolide polyene antibiotics, amphotericin-B, nystatin, and candicidin are preferred.

The water-soluble compositions of the present invention contain a bioactive lipophilic compound and a solubilizing agent in a molar ratio of approximately 1:1 to 1:5. The molar ratio of about 1:2 is preferred. The upper limit of the molar ratio is not critical, and the solubilizing agent can be used in any excess. This is not desirable, however, as increasing the amount of the solubilizing agent decreases the concentration of the active ingredient in the composition and in its aqueous solutions.

The water-soluble compositions of the present invention can be prepared by two different procedures, either in the presence or in the absence of an auxiliary organic solvent. In the first case, a lipophilic compound and a solubilizing agent are first dissolved in a predetermined molar ratio in a water-miscible organic solvent and this solution is then diluted with a predetermined amount of water, without precipitation of the lipophilic compound. The organic solvent and water are then removed by evaporation under reduced pressure. A volatile organic solvent is usually removed first, followed by water, in which case the amount of water removed from the solution may be controlled, to achieve a desired concentration of the water-soluble composition in the remaining concentrate. Alternatively, both the organic solvent and water are removed by evaporation, and the waxy residue is reconstituted with a suitable aqueous medium (such as water, physiological saline, or a buffer solution), to provide a clear aqueous solution.

The organic solvent used is in the above procedure should be a good solvent for both the lipophilic compound and the solubilizing agent and has to be miscible with water. If a water-soluble compositions is to be used in a pharmaceutical formulation, this solvent should be also pharmaceutically acceptable, as the removal of the solvent by evaporation may not always be possible. Examples of solvents suitable for the practice of the invention are tetrahydrofuran, ethanol, ethylene glycol, propylene glycol, and acetic acid. Solvents with a low boiling point, such as tetrahydrofuran, are preferred.

The amount of the organic solvent is not critical, and is equal to or greater than the minimum amount of solvent necessary to dissolve the given amounts of the lipophilic compound and solubilizing agent. The amount of water used for the dilution is also not critical, and is preferably between 10 to 25 times the volume of the organic solvent.

An alternative procedure for preparing water-soluble compositions according to the invention consists of preparing first a mixture of a lipophilic compound and a solubilizing agent in a predetermined molar ratio. This mixture is then heated to a temperature higher than the respective melting points of the lipophilic compound and the solubilizing agent, for a time necessary to obtain a clear melt, which process can be seen as a dissolution of the lipophilic compound in the solubilizing agent. The melt so obtained can be reconstituted with a predetermined amount of a suitable aqueous medium, to provide a clear aqueous solution of a desired concentration. This method of preparing water-soluble compositions of the invention is preferred, as it is simpler and avoids limitations of the procedure that relies on an auxiliary organic solvent, such as the pharmaceutically acceptable character of the solvent required for most applications.

The ability of solubilizing agents of the present invention to dissolve lipophilic compounds in the absence of an auxiliary organic solvent can be used for preparing water-soluble forms of bioactive compounds, in particular Coenzyme $Q_{10}$, without purifying it by crystallization after synthesis, thus reducing the overall cost of preparing water-soluble compositions of this compound.

Many compositions of the present invention show a decreasing solubility in water with increasing temperature of the solution. This provides an alternative method of isolation and/or purification of such compositions. For the purpose of purification, the composition is dissolved in water at a ratio of the composition to water not exceeding 1:2 by volume and the solution is heated, for example in a boiling water bath, for a time necessary to achieve the separation of the water-soluble composition as a liquid phase, usually a few minutes. The oily phase is then separated from the hot solution, while keeping the temperature of the solution substantially unchanged, as cooling of the solution would increase the solubility of the composition and result in a reduced yield of the recovery. A speedy separation of the oily phase to avoid the cooling can be achieved, for example, by centrifugation.

The water-soluble compositions of the present invention have a waxy consistence and may be difficult to manipulate in this highly concentrated form. To make them more easily processable as solids, they may be combined with a suitable solid, water-soluble additives, such as vitamin C, gelatin, a protein supplement, or a polyethylene glycol. In the latter case, a polyethylene glycol having an average molecular weight greater than about 5000 is preferred. The ratio of the composition and the additive is not critical, but will be usually limited to avoid an unnecessary dilution of the active ingredient by the additive. Such solid composition are particularly useful for the preparation of certain dosage forms of bioactive compounds, such as tablets or granulates.

The compositions of the present invention show an excellent solubility in water and allow the preparation of aqueous solutions of almost any concentration. As the concentrated solutions can be diluted with an aqueous medium in any proportion and over a wide range of pH conditions without precipitation of the lipophilic compound, the solubility of the compound is maintained under physiological conditions, for example after an oral or parenteral administration of the composition. This normally results in an improved bioavailability of the compound.

The compositions of the present invention and aqueous solutions thereof show an excellent stability over long periods of time (several months at room temperature, at least one year when refrigerated, or indefinitely when frozen) and over wide ranges of temperature and pH conditions (temperatures from −80° C. to 120° C., pH from 2.0 to 8.0). Aqueous solutions can be repeatedly frozen and thawed without any perceptible degradation. The stability under high temperature conditions allows an easy sterilization of the solutions, without compromising the solubility of the active ingredient.

The water-soluble compositions of the present invention can be easily incorporated into pharmaceutical or cosmetic formulations, which are then charcterized by an improved bioavailability of the lipophilic active ingredient. Such formulations may further contain additional active ingredients and/or a pharmaceutically or cosmetically acceptable additives or vehicles, including solvents, adjuvants, excipients, sweeteners, fillers, colorants, flavoring agents, lubricants, binders, moisturizing agents, preservatives and mixtures thereof. The formulations may have a form suitable for a topical (e.g., a cream, lotion, gel, ointment, dermal adhesive patch), oral (e.g., a capsule, tablet, caplet, granulate), or parenteral (e.g., suppository, sterile solution) administration. Among the acceptable vehicles and solvents that may be employed for administration by injection are water, mildly acidified water, Ringer's solution and isotonic sodium chloride solution.

Among water-soluble compositions and pharmaceutical and cosmetic formulations, those comprising Coenzyme $Q_{10}$ are of particular interest. Coenzyme $Q_{10}$ is a natural compound whose therapeutic potential has been recently recognized for a number of conditions and disorders related to mitochondrial dysfunctions and/or tissue damage caused by free radicals and oxidants. These include, but are not limited to: cardiovascular diseases (e.g., congestive heart failure), muscular disorders (e.g., muscular dystrophy), mitochondrial encephalomyolopaties (i.g., MELAS, KSS), neurodegenerative disorders (e.g., Alzheimer', Parkinson's, Huntington's diseases), restoration of immune deficiencies caused by drugs or infections (AIDS, allergies, cancer). Of particular interest is the clinical use of Coenzyme $Q_{10}$ to minimize tissue damage resulted from ischemia/reperfusion (e.g., stroke, head trauma, angioplasty, organ transplantation, surgery in general). Another area of interest is the use of Coenzyme $Q_{10}$ in therapy as adjuvant, for example for infectious diseases, in combination with cholesterol-lowering drugs for the treatment of hypercholesteremia, or in combination with chemotherapeutic agents in the treatment of cancers. Coenzyme $Q_{10}$ is also of great interest to cosmetic industry, as an agent slowing down natural skin ageing processes. Water-soluble compositions comprising a macrolide polyene antibiotic, such as amphotericin-B, nystatin, or candicidin, are of particular interest for the treatment of fungal infections, including fungal infections in immunocompromised patients.

Bioactive lipophilic compounds in the form of a water-soluble composition according to the present invention may be administered to a warm-blooded animal, particularly a human, in need of the prophylaxis or therapy. The dose of a bioactive lipophilic compound and the corresponding dose of its water-soluble composition for treating the above-mentioned diseases or disorders vary upon the manner of administration, the age, sex, the body weight of the subject, and the condition being treated, and will be ultimately decided by the attending physician or veterinarian. Such an amount of the bioactive compound in the form of its water-soluble composition as determined by the attending physician or veterinarian is referred to herein as a "therapeutically effective amount".

The biological activity of Coenzyme $Q_{10}$ is believed to be linked to its ability to act as an antioxidant and free radical scavenger protecting integrity of cell membranes and to offset the inability of diseased cells to manufacture sufficient energy for cellular repair, by stimulating the mitochondrial respiration and production of ATP. For effectiveness in both clinical and cosmetic applications, preparations of Coenzyme $Q_{10}$ with high bioavailability and solubility in aqueous media are normally desirable.

Most pharmaceutical and cosmetic formulations proposed to date for Coenzyme $Q_{10}$ suffer from a number of drawbacks, such as the use of components causing an undesirable immune response when administered parenterally or gastric disorders when administered orally. Some formulations are stable only over a narrow range of pH values and most are characterized by a poor bioavailability of the active component (Coenzyme $Q_{10}$). In particular, there are no reliable formulations for intravenous administration of Coenzyme $Q_{10}$, as there are no formulations universally applicable to topical, oral, and parenteral administration routes. The water-soluble compositions of the present invention comprising Coenzyme $Q_{10}$ are free of the above drawbacks and can be incorporated into pharmaceutical formulations suitable for all administration routes, topical, oral, and parenteral, which are stable and characterized by a good solubility and bioavailability of the active component.

The invention further provides novel solubilizing agents of the general formula $$\{X\text{—}OOC\text{—}[(CH_2)_n\text{—}COO]_m\}_p\text{—}Y \quad (I)$$

wherein:
X is a residue of a hydrophobic moiety,
Y is a residue of a hydrophilic moiety,
p is 1 or 2,
m is 0 or 1, and
n is an integer greater than or equal to 0,
provided that:
when p and m are both equal to 1 and the hydrophobic moiety is cholesterol, n is greater than 4 and not equal to 8, and
when p and m are both equal to 1 and the hydrophobic moiety is a-(+)-tocopherol, n is not equal 2,
and wherein X and Y have the earlier discussed meaning.

Compounds excluded by the proviso are known in the prior art, in particular polyoxyethanyl-cholesteryl sebacate (PCS) and polyoxyethanyl-a-tocopheryl succinate (TPGS).

The compounds of formula (I) can be prepared by standard methods of synthetic organic chemistry, well known to those skilled in the art. In particular, compounds where p is equal to 1 or 2 and m is equal to 1 can be prepared by reacting a compound of the general formula X—OH with a compound of the general formula Z—OC—$(CH_2)_n$—CO—Z, where Z is a leaving group, and further reacting the product so obtained with a compound of the general formula HO—Y—OR, wherein R is hydrogen or an alkyl, and X, Y and n are as defined hereinbefore. Halogens, in particular Cl and Br, are preferred as the leaving group Z. Hydrogen and a lower alkyl ($C_1$-$C_4$) are preferred for R.

Many solubilizing agents of formula (I) show a decreasing solubility in water with the increasing temperature of the solution, which provides a convenient method of purification of these compounds. The steps and conditions of the purification process are substantially the same as those discussed above for the purification of water-soluble compositions of the invention.

Various aspects of the present invention will be further illustrated by the following non-limiting examples.

EXAMPLES

The following abbreviations are used throughout the Examples:
CoQ$_{10}$, CoQ$_{10}$—Coenzyme Q$_{10}$
PCS—polyoxyethanyl-cholesteryl sebacate
PTS—polyoxyethanyl-a-tocopheryl sebacate
PSS—polyoxyethanyl-sitosteryl sebacate
PTD—polyoxyethanyl-a-tocopheryl dodecanodioate
PTSr—polyoxyethanyl-a-tocopheryl suberate
PTAz—polyoxyethanyl-a-tocopheryl azelaate
TPGS—polyoxyethanyl-a-tocopheryl succinate A number following one of the above abbreviations (e.g., PCS-600) indicates an average molecular weight of the polyoxyethanyl moiety of the compound. A number followed by Me abbreviation (e.g., PTS-750Me) indicates a polyoxyethanyl moiety capped with a methyl group (methoxypolyoxyethanyl).

Examples 1 and 2 illustrate methods of preparation of solubilizing agents of the present invention.

Example 1

Preparation of Polyoxyethanyl-sitosteryl Sebacate (PSS-600)

0.83 g of b-sitosterol (Sigma Chem. Co., product #S-5753, approximately 60%) was dissolved in 3 ml of dry toluene at 40° C., followed by addition of 1.33 mmole of triethylamine (TEA). 1.33 mmole of sebacoyl chloride dissolved in 2 ml of dry toluene was than added (dropwise, while stirring, and under anhydrous conditions) to the b-sitosterol-TEA solution. The reaction was carried out for 10 min at room temperature, at which time 2 mmole of PEG-600 (polyethylene glycol, Sigma Chem. Co., product # P-3390) and 2.66 mmole of TEA dissolved in 3 ml of dry toluene were added dropwise to the reaction mixture. The reaction was continued with stirring for additional 20 min at room temperature and the reaction mixture was extracted four times with 3 ml each time of saturated solution of NaCl. The toluene was removed under reduced pressure leaving a waxy residue. This product was dissolved in 15 ml of water and water-insoluble materials removed by filtration. The filtrate was lyophilized, yielding 0.8 g of pale-yellow waxy product (PSS-600). The same method was used for the preparation of polyoxyethanyl-cholesteryl sebacate (PCS-600).

Example 2

Preparation of Polyoxyethanyl-a-tocopheryl Sebacate (PTS-600)

A solution of 1 mmole of a-tocopherol (Sigma Chem. Co., product # T-3251) and 1.33 mmole of TEA in 3 ml of dry toluene was added (dropwise, under anhydrous conditions, while stirring) to 1.33 mmole of sebacoyl chloride dissolved in 2 ml of dry toluene. The reaction was carried out for 10 min at room temperature, followed by a dropwise addition of 2 mmole of PEG-600 (polyethylene glycol, Sigma, P-3390) and 2.66 mmole of TEA dissolved in 3 ml of toluene. The reaction was continued for additional 20 min at room temperature with constant stirring. The reaction mixture was extracted four times with 3 ml each time of saturated solution of NaCl and toluene evaporated under a reduced pressure. The product was dissolved in 5 ml of water and the residual toluene was further removed by co-evaporation with water under a reduced pressure. The final waxy product (1.15 g) was obtained by lyophilization.

Other solubilizing agents (Table 1) were obtained by linking polyethylene glycol (average molecular weight 1000, Sigma Chem. Co., product # P-3515) or methoxypolyethylene glycol (average molecular weight 750, Sigma Chem. Co., product # M-7018) to a-tocopherol using adipoyl, suberoyl, azelaoyl or dodecanedioyl dichlorides. They were synthesized according to the method of Example 2 and their identities were confirmed by mass spectrometry analysis applying MALDI-TOF technique.

Example 3 provides molecular characteristics of the synthesized solubilizing agents.

Example 3

Molecular Characteristic of Solubilizing Agents Obtained by MALDI-TOF Mass Spectrometry

TABLE 1

Molecular mass of synthesized solubilizing agents

| Solubilizing agent | Molecular mass m/z |
|---|---|
| PSS-600 | 1194.3 ± 44 |
| PCS-600 | 1166.1 ± 44 |
| PTS-600 | 1209.7 ± 44 |

TABLE 1-continued

Molecular mass of synthesized solubilizing agents

| Solubilizing agent | Molecular mass m/z |
|---|---|
| PTD-600 | 1237.5 ± 44 |
| PTS-750Me | 1355.7 ± 44 |
| PTD-750Me | 1383.7 ± 44 |
| PTS-1000 | 1605.9 ± 44 |
| PTSr-600 | 1181.6 ± 44 |
| PTSr-1000 | 1578.2 ± 44 |
| PTAz-600 | 1195.8 ± 44 |
| PTA-600 | 1153.5 ± 44 |
| PTSc-600 | 1125.7 ± 44 |

Example 4 illustrates a method of purification of solubilizing agents.

Example 4

Purification of Solubilizing Agents

A solubilizing agent prepared according to Examples 1 or 2 was dissolved in water at 2:1 v/v ratio. The solution was heated in a boiling water bath for approximately 2 min, until a visible precipitation occurred. This was followed by a brief centrifugation (at least 2000×g) of the hot mixture to achieve separation of the precipitated product which is insoluble in hot water. The water phase (supernatant) was removed by decantation leaving a clear pellet of the product containing approximately 10% of water.

Examples 5 and 6 illustrate a preparation of water-soluble Coenzyme Q10 compositions by a direct admixing of the two components.

Example 5

Direct Preparation of Tocopherol-based Water-soluble Compositions of Coenzyme $Q_{10}$

TABLE 2

Components of tocopherol-based water-soluble Coenzyme $Q_{10}$ compositions

| Coenzyme $Q_{10}$ | 0.01 | g |
|---|---|---|
| TPGS | 0.035 | g |
| Coenzyme $Q_{10}$ | 0.01 | g |
| PTS-600 | 0.03 | g |
| Coenzyme $Q_{10}$ | 0.01 | g |
| PTD-600 | 0.03 | g |
| Coenzyme $Q_{10}$ | 0.01 | g |
| PTS-750Me | 0.03 | g |
| Coenzyme $Q_{10}$ | 0.01 | g |
| PTD-750Me | 0.03 | g |
| Coenzyme $Q_{10}$ | 0.01 | g |
| PTS-1000 | 0.03 | g |
| Coenzyme $Q_{10}$ | 0.01 | g |
| PTSr-1000 | 0.03 | g |
| Coenzyme $Q_{10}$ | 0.01 | g |
| PTSr-600 | 0.03 | g |
| Coenzyme $Q_{10}$ | 0.01 | g |
| PTAz-600 | 0.03 | g |

Table 2 shows amounts of starting materials used for the preparation of a-tocopherol-based water-soluble compositions of Coenzyme $Q_{10}$. In each case the two components were admixed together at a predetermined ratio and were heated to a temperature higher than their melting points, typically 60° C.–80° C., until the components melted together and formed a clear, transparent and uniform melt. The optimal ratio of a solubilizing agent to Coenzyme $Q_{10}$ was found to be 2:1 mol/mol or 3:1 w/w. These compositions could be stored in sealed vials for at least 2–3 years when refrigerated. They could be reconstituted at any time with water or physiological solution of saline (0.9%), at any ratio, and they remained water soluble and stable for several month when refrigerated or frozen.

Example 6

Direct Preparation of Sterol-based Water-soluble Compositions of Coenzyme $Q_{10}$

TABLE 3

Components of sterol-based water-soluble Coenzyme $Q_{10}$ compositions

| Coenzyme $Q_{10}$ | 0.01 | g |
|---|---|---|
| PCS-600 | 0.03 | g |
| Coenzyme $Q_{10}$ | 0.01 | g |
| PSS-600 | 0.03 | g |

Table 3 shows amounts of starting materials used for the preparation of sterol-based, water-soluble compositions of Coenzyme $Q_{10}$. In each case the two components were admixed at a predetermined ratio (the optimal ratio of a solubilizing agent to CoQ10 was found to be 2:1 mol/mol or 3:1 w/w) and were heated to a temperature higher than their melting points, typically 60° C.–80° C., until the components melted together and formed a clear transparent liquid. The liquid was dissolved in water (at a ratio 2:1 v/v) and the solution was heated in a boiling water bath for approximately 2 minutes, until clear waxy precipitate was formed. The precipitate could than be separated from the hot solution by centrifugation at 2000×g. To achieve its full water solubility at room temperature, the cycle of heating, centrifugation and cooling to room temperature, without removal of supernatant between the cycles, was repeated 2 to 3 times. After the final centrifugation, the hot supernatant was decanted and clear transparent pellet of the product was recovered. The compositions could be stored refrigerated in sealed vials for at least 2–3 years. Aqueous solutions (in water or saline) of the above compositions could be prepared and they were stable for several months when refrigerated.

Examples 7, 8 and 9 illustrate preparation of water-soluble Coenzyme Q10 compositions in the presence of an auxiliary solvent.

Example 7

Solvent-based Preparation of Water Soluble Compositions of Coenzyme $Q_{10}$

TABLE 4

Components of water-soluble compositions of Coenzyme $Q_{10}$

| Coenzyme $Q_{10}$ | 5 | g |
|---|---|---|
| PCS-600 | 15 | g |
| THF | 30 | ml |
| $H_2O$ | 400 | ml |
| Coenzyme $Q_{10}$ | 0.01 | g |
| PSS-600 | 0.03 | g |
| THF | 0.1 | ml |
| $H_2O$ | 2.5 | ml |
| Coenzyme $Q_{10}$ | 0.3 | g |
| PTS-600 | 1.0 | g |

TABLE 4-continued

Components of water-soluble compositions of Coenzyme $Q_{10}$

| | | |
|---|---|---|
| THF | 4.0 | ml |
| $H_2O$ | 60.0 | ml |
| Coenzyme $Q_{10}$ | 0.01 | g |
| PTD-600 | 0.03 | g |
| THF | 0.1 | ml |
| $H_2O$ | 2.5 | ml |
| Coenzyme $Q_{10}$ | 0.01 | g |
| PTS-750Me | 0.03 | g |
| THF | 0.1 | ml |
| $H_2O$ | 2.5 | ml |
| Coenzyme $Q_{10}$ | 0.01 | g |
| PTD-750Me | 0.03 | g |
| THF | 0.1 | ml |
| $H_2O$ | 2.5 | ml |

Table 4 shows amounts of starting materials used for various water-soluble Coenzyme $Q_{10}$ compositions. In each case Coenzyme $Q_{10}$ and a solubilizing agent were both dissolved in tetrahydrofuran (THF) and the solution was added to water with vigorous stirring, while maintaining the temperature of the mixture close to 0° C. The solvent and a part of water were then evaporated under a reduced pressure to obtain a desired concentration of Coenzyme $Q_{10}$, usually 80–100 mg/ml. These compositions could be stored refrigerated for at least 2–3 years and could be reconstituted with aqueous media (water, saline) to a desired final concentration of Coenzyme $Q_{10}$ in the water-soluble form. Compositions with higher concentrations of Coenzyme $Q_{10}$ (up to 200 mg/ml) were also obtained by following this procedure.

Example 8

Solvent-based Preparation of Water-soluble TPGS—Coenzyme $Q_{10}$ Composition

TABLE 5

Components of water-soluble TPGS-Coenzyme $Q_{10}$

| | | |
|---|---|---|
| Coenzyme $Q_{10}$ | 0.01 | g |
| TPGS | 0.035 | g |
| THF | 0.1 | ml |
| $H_2O$ | 2.5 | ml |

Table 5 shows amounts of starting materials used for water-soluble TPGS-Coenzyme $Q_{10}$ composition which was prepared according to the procedure described in Example 7. However, this product did not precipitated from an aqueous solution after heating. Water and the solvent could be removed by evaporation under a reduced pressure. Water solubility and stability of the composition was the same as those described in Examples 4 and 5.

Example 9 describes a procedure for the preparation of water-soluble ubiquinol compositions.

Example 9

Preparation of Water-soluble Ubiquinol Compositions

TABLE 6

Components of water-soluble ubiquinol compositions

| | | |
|---|---|---|
| Ubiquinol 50 | 0.3 | g |
| TPGS | 0.9 | g |

TABLE 6-continued

Components of water-soluble ubiquinol compositions

| | | |
|---|---|---|
| Ubiquinol 50 | 0.3 | g |
| TPGS | 0.9 | g |
| Propylene Glycol usp. | 0.9 | ml |
| Ubiquinol 50 | 0.1 | g |
| Coenzyme $Q_{10}$ | 0.1 | g |
| PTS-600 | 0.5 | g |
| Ubiquinol 50 | 0.1 | g |
| Coenzyme $Q_{10}$ | 0.1 | g |
| Vitamin E | 0.001 | g |
| PTS-600 | 0.5 | g |

Table 6 shows amounts of starting materials used for water-soluble ubiquinol (a reduced form of Coenzyme $Q_{10}$) compositions. Ubiquinol was first prepared by the following method. 0.3 g of Coenzyme $Q_{10}$ and 0.2 g of zinc dust were suspended in 2.5 ml of glacial acetic acid. The mixture was placed in 50° C. water bath, with occasional shaking, for approximately 15 min. The reaction mixture was diluted with 2.5 ml of water and extracted twice with 5 ml of hexane. The hexane extracts were combined, washed twice with 2.5 ml of water, dried over anhydrous magnesium sulfate, evaporated under reduced pressure and finally under a high vacuum. The resulting white waxy residue of ubiquinol was combined with 0.9 g of TPGS and it was heated to 60° C.–80° C. until the mixture melted and became clear. Upon reconstitution with water an opaque solution was formed. This composition remained unchanged for up to 2 months when sealed under argon and frozen. The water solubility of this composition could be improved by admixing with propylene glycol at a ratio given in the Table 6. The aqueous (water and saline) solutions of this composition were stable and could be stored sealed under argon when frozen.

Examples 10 and 11 illustrate preparation of water soluble vitamin E and b-carotene compositions.

Example 10

Preparation of Water-soluble Formulations of Vitamins

TABLE 7

Components of water-soluble compositions of vitamin E and b-carotene

| | | |
|---|---|---|
| Vitamin E | 0.10 | g |
| PTS-600 | 0.60 | g |
| Vitamin E | 0.22 | g |
| PCS-600 | 1.00 | g |
| THF | 2.50 | ml |
| $H_2O$ | 35.00 | ml |
| Vitamin E | 0.025 | g |
| PTS-600 | 0.150 | g |
| THF | 0.125 | ml |
| $H_2O$ | 2.0 | ml |
| Provitamin A (b-carotene) | 0.01 | g |
| PTS-600 | 0.50 | g |
| THF | 0.20 | ml |
| $H_2O$ | 3.0 | ml |

Table 7 shows amounts of starting materials used for various compositions prepared by direct admixing method (Example 5) or with the aid of an auxiliary solvent (Example 7). The optimal ratio of a solubilizing agent to Vitamin E was found to be 2:1 mol/mol or 6:1 w/w. The concentrated compositions could be stored refrigerated for up to 2 years. The aqueous solutions (in water or saline) were also stable and could be stored frozen.

Example 11 illustrates methods for isolation, concentration and sterilization of the compositions according to the present invention.

Example 11

Isolation, Concentration and Sterilization of Water-soluble Compositions

According to the present invention, two processes can be applied for the preparation of water-soluble compositions of lipophilic compounds: (i) a lipophilic compound and a solubilizing agent can either be combined directly and melted together, or (ii) the two are first dissolved in a water-miscible auxiliary solvent, the solution mixed with water and both the solvent and the excess of water are removed by evaporation. The obtained compositions are soluble in aqueous media at room temperature, but not at temperatures higher than approximately 80° C. They precipitate out of water when heated, but return to the solution upon cooling. This provides a simple, effective and inexpensive method of their isolation, concentration and sterilization.

Typically, the aqueous solutions of the compositions (with the exception of TPGS-Coenzyme $Q_{10}$, Example 9) are heated in a boiling water bath for about 2 min or until visible precipitate is formed. The separation of the precipitates from the hot water is accelerated by a rapid centrifugation at 2000×g g. The water phase is decanted and the obtained waxy, transparent composition can be stored refrigerated in sealed vials. It remains stable for at least 8 month and can be further diluted with aqueous media (water, saline or a buffer). When refrigerated, these solutions are stable for at least 3 years. The process of precipitation/solubilization is reversible and repeating it several times improves the stability of diluted aqueous solutions of the composition. If precipitation of the composition occurs during storage, its solubility can be restored by applying the above heating/centrifugation cycle. The compositions are also suitable for injections, since the described process can be applied for their sterilization.

Example 12 illustrates the preparation of dry powder compositions containing Coenzyme $Q_{10}$.

Example 12

Preparation of Dry Powder Coenzyme $Q_{10}$ Compositions

TABLE 8

Components of dry powder Coenzyme $Q_{10}$ compositions

| | |
|---|---|
| CoQ10/PCS-600 composition containing 40 mg of CoQ10/ml of water | 0.07 g CoQ10/0.21 g PCS-600 |
| BSA (0.25 g/ml of water) | 0.25 g |
| CoQ10/PCS-600 composition containing 40 mg of CoQ10/ml of water | 0.07 g CoQ10/0.21 g PCS-600 |
| Gelatin (0.125 g/ml in water) | 0.25 g |
| CoQ10/PCS-600 composition containing 40 mg of CoQ10/ml of water | 0.03 g CoQ10/0.09 g PCS-600 |
| Vitamin C (0.25 g/ml in water) | 0.50 g |

Table 8 shows amounts of starting materials used for the preparation of dry powder compositions of Coenzyme $Q_{10}$. The aqueous solutions of the above components were combined and lyophilized. The resulting powdered products could be pressed into tablets which remained stable and water-soluble.

Example 13 illustrates the preparation of dry powder compositions containing multiple components.

Example 13

Preparation of Compositions Containing Coenzyme $Q_{10}$, Vitamin E and Vitamin C

TABLE 9

Components of water soluble complex compositions

| | |
|---|---|
| Coenzyme Q10/PTS-600 composition (containing 40 mg of CoQ10/ml of water) | 0.03 g CoQ10/0.09 g PTS-600 |
| Vitamin E/PTS-600 composition (containing 20 mg of vitamin E/ml) | 0.005 g Vit E/0.025 g PTS-600 |
| Vitamin C (0.25 g/ml in water) | 0.75 g |

Table 9 shows amounts of starting materials used. The aqueous solutions of the above components were combined and lyophilized. The resulting powdered products could be pressed into tablets which remained stable and water-soluble.

Example 14 demonstrates the lack of toxicity of solubilizing agents.

Example 14

In Vitro Toxicity Study

Stock solutions of solubilizing agents (1 mg/ml in PBS) were prepared and were added directly to lymphocytic Jurkat and neuroblastoma NT2 cell cultures in the amounts required to achieve a final concentration in the medium of 200, 100 and 50 mg/ml and cell viability was assessed by trypan blue exclusion assay. The results of assessment are shown in FIG. 1.

Figure 2:
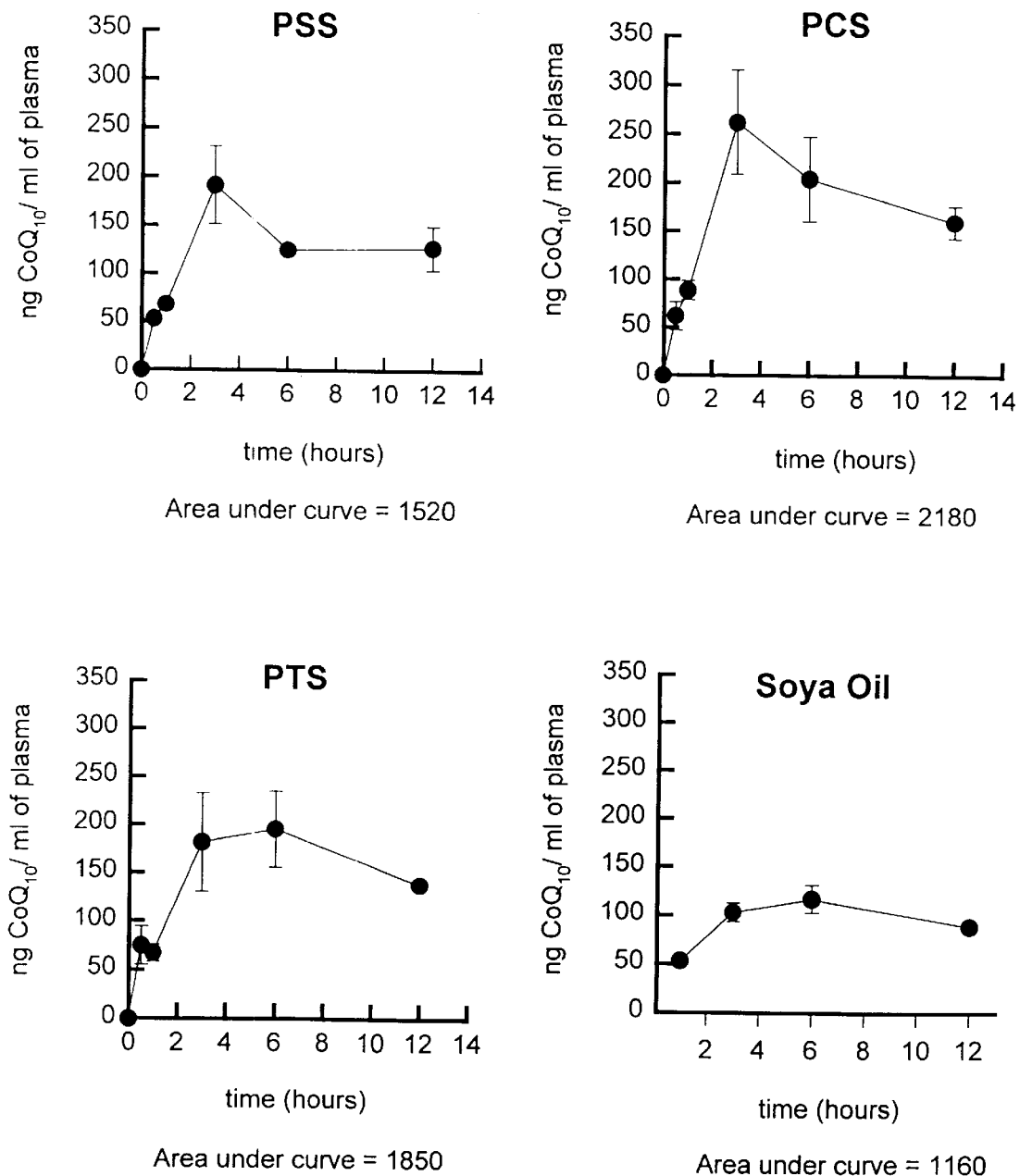
FIG. 2 is a graph showing the bioavailability of $CoQ_{10}$ in various water-soluble compositions.

With the exception of commercially available TPGS, none of the solubilizing agents of the invention had adverse effects on either cell growth or viability in vitro when added to cell cultures at concentrations up to 200 mg/ml. Also, no toxicity was observed when the compositions containing CoQ10 and PTS, PCS or PSS were given to Sprague Dawley rats at concentrations up to 20 mg/kg body weight, as shown in FIG. 2

Although no rationale can be provided to explain the toxicity of TPGS observed in the experimental paradigm used, its usefulness as a solubilizing agent in pharmaceutical formulations should be further investigated and should be taken with caution.

Example 15 illustrates improved bioavailability of water-soluble forms of CoQ10.

Example 15

Bioavailability of Water-soluble Forms of Coenzyme $Q_{10}$

CoQ10, in the form of either water-soluble or oil-soluble compositions, was administered by gavage to 300–350 g male Sprague Dawley rats at a dose of 6 mg/kg body weight. Blood samples were collected and CoQ10 content was measured in plasma by the HPLC method which we have developed for analysis of CoQ10 in biological samples (Graves et al., Analysis of CoEnzyme Q10 content in human plasma and other biological samples. In: Free Radicals and Antioxidant Protocols, Ed. D. Armstrong, Humana Press. pp: 353–365, 1998).

Briefly, 0.1 ml sample of plasma or lysed cells (Examples 15 and 16), was mixed with 0.33 ml of 1-propanol, vortexed for 30 sec and left to stand at room temperature for 1 min. 0.86 ml of n-hexane were than added, the sample was vigorously vortexed for 30 sec, and centrifuged to achieve a phase separation and to pellet the denatured proteins. The upper phase which consisted of n-hexane and 1-propanol and contained $CoQ_{10}$ was collected and evaporated to dryness under argon. The remaining dry residue was redissolved in 60 ml of ethanol and 2 ml of $H_2O_2$ in order to convert all $CoQ_{10}$ to its oxidized form. Sample aliquots were analysed by a reverse-phase chromatography on a Supelcosil LC-18-DB column (5 mm particle size, 30 cm×4.0 mm I.D., Supelco) with the mobile phase of ethanol:methanol 80:20 (v/v) at the flow rate of 1 ml/min. Absorbance at 275 and 290 nm was monitored.

A standard calibration curve of CoQ10 and Beckman System Gold Software were utilized for data quantification. The amount of Coenzyme $Q_{10}$ was calculated according to measured peak-areas of analysed samples. The calibration curve was prepared from a CoQ10 ethanol solution of a concentration determined spectrophotometrically from its extinction coefficient of =14,200 at 275 nm. The ethanol solution of CoQ10 can be stored in sealed amber vials at $-20°$ C.

The data presented in FIG. 2 show significantly improved (by 1.5 to 2 fold) bioavailability of CoQ10 when given orally as a water soluble compositions in comparison with the oil formulation. Significantly, the kinetics of the uptake is much faster (plasma level peaked at about 3 hr) and the maximal plasma levels achieved are also much higher (by 2 fold) when CoQ10 is given in the water soluble form.

Example 16 illustrates the ability of cells to internalize the water-soluble form of CoQ10.

Example 16

Intracellular Uptake of Coenzyme $Q_{10}$

The following experiments were designed to demonstrate the ability of human keratinocytes to internalize exogenous CoQ10. Human skin keratinocytes (ATCC CRL-8858), were cultured in SFM (serum free medium, Gibco BRL, cat no. 10724) supplemented with 0.2 ng/ml of EGF (epidermal growth factor), 30 mg/ml of bovine pituitary extract and different concentrations of CoQ10 which was added directly to the tissue culture medium in a form of water soluble PCS formulation. The cells were grown for up to 3 days under these conditions, then harvested and washed extensively. The cells (approximately $1-3\times10^6$/per sample) were resuspended in $ddH_2O$ and were broken by an osmotic shock after a freezing and thawing cycle. CoQ10 was extracted by a propanol:hexane solvent mixture and its content was measured by the HPLC described above.

In order to obtain the mitochondrial fraction, the cells were homogenized in a buffer containing 250 mM sucrose, 50 mM Tris-HCl pH 7.4, 5 mM $MgCl_2$ and 1 mM EDTA. The homogenates were centrifuged at 800 g for 10 min at 4° C. The supernatants were collected and were further centrifuged at 10,000 g for 10 min at 4° C. The pellets, representing crude mitochondrial fractions, were resuspended in 100 ml of $ddH_2O$, extracted with a propanol/hexane solvent mixture and processed for CoQ10 analysis.

TABLE 10

Intracellular uptake of $CoQ_{10}$ by cultured human keratinocytes

| $CoQ_{10}$ added mg/ml of media | Total cellular $CoQ_{10}$ content ng/$10^6$ cells |
|---|---|
| 0 - control | 10 |
| 10 | 21.1 |
| 100 | 49.6 |

The data summarized in Table 10 show the intracellular uptake of CoQ10 by human keratinocytes from the aqueous environment of tissue culture media. During the 3-day experimental period the intracellular content of CoQ10 increased approximately 2-fold and 5-fold from the media containing 10 mg/ml and 100 mg/ml of CoQ10 resuspended in the PCS formulation, respectively.

TABLE 11

Increased mitochondrial $CoQ_{10}$ content in keratinocytes

| $CoQ_{10}$ added mg/ml of media | Total cellular $CoQ_{10}$ content ng/$10^6$ cells | Total mitochondrial content ng/$10^6$ cells |
|---|---|---|
| 0 | 11 | 1 |
| 10 | 69 | 9.8 |

The results shown in Table 11 demonstrate a significant increase of CoQ10 content in the mitochondrial fraction of cells grown for 3 days in the presence of 10 mg/ml of CoQ10. It is expected that, in addition to its function as lipid-soluble antioxidant, the elevated CoQ10 content, particularly in the mitochondria, will potentiate the efficiency of the energy producing respiratory chain which is pivotal for the cellular viability.

Example 17 serves to demonstrate the ability of CoQ10 to increase the efficiency of mitochondrial respiratory chain to produce more ATP.

Example 17

Effects of Coenzyme $Q_{10}$ on Cellular ATP Content in Human NT2 Cells

Human teratocarcinoma NT2 (Stratagene, San Diego, Calif.) were grown in DME medium (GiBco BRL) supplemented with 10% FBS (fetal bovive serum) and 10 mg/ml of CoQ10 which was added directly to the tissue culture medium in a form of water soluble PTS formulation. The cells were harvested at 24 hour intervals, resuspended in a buffer consisting of 0.02M glycine, 0.05M $MgSO_4$, 0.004M EDTA, pH7.4 and aliquoted into 100 $\mu L$ samples.

The ATP content was measured using a luciferin-luciferase bioluminescence assay (Sigma, St. Louis, Mo.). Luciferase catalyses the decarboxylation of luciferin and the hydrolysis of ATP to give pyrophosphate and oxyluciferin. These reactions result in emission of light at 560 nm. The intensity of the emitted light is proportional to the ATP concentration. The ATP assay was carried out by mixing 100 $\mu L$ of sample with 75 $\mu L$ of a 0.5 mg/mL solution of luciferase-luciferin. Emitted light was detected using a Beckman LS 3801 scintillation counter. A standard curve was prepared ranging from 10 to 100 pmols of ATP. ATP levels were expressed as pmols ATP/$\mu g$ protein.

FIG. 3 shows the effect of PTS-CoQ10 composition on cellular ATP level in NY2 cells. The ATP level was reproducibly higher in cells that were cultured for 3 days in the presence of water soluble PTS-CoQ10 formulation. The data points represent mean values from three separate experiments +/−SEM.

Example 18 shows protective effects of CoQ10 against hypoxia in human neuroblastoma NT2 cells.

Example 18

Protection Against Hypoxia

Human teratocarcinoma NT2 (Stratagene, San Diego, Calif.) were seeded into 25 cm$^2$ tissue culture flasks (at a density of 0.3×10$^6$ cells/ml) and were grown for 3 days in DME medium (Gibco BRL) supplemented with 10% FBS and in the presence or absence of either 10 mg/ml of CoQ10-PTS formulation added directly to the tissue culture media. The flasks were sealed in an anaerobic chamber containing Gas Pak Plus gas generator envelopes and were incubated in the anaerobic conditions at 37° C. for 17.5 hours in glucose-free medium. Following the hypoxic treatment the cells were placed again in the complete medium (with and without CoQ10 or vitamin E) and were analysed either immediately (time 0) or were cultured for the additional 24 hr under the normoxic conditions. Cell viability was measured by trypan blue exclusion assay. The results are shown in FIG. 4.

The protective effects of CoQ10 against hypoxia in NT2 cells is clearly evident. Approximately 50% less cells pretreated for 3 days with PTs-CoQ10 died during the 24 hr recovery period from hypoxia as compared to the cells which did not receive CoQ10.

Example 19 shows that CoQ10 is equally effective in protecting cells against cell death triggered by hypoxia as vitamin E.

Example 19

Comparison of Coenzyme Q10 and Vitamin E Anti-oxidant Function

Human teratocarcinoma NT2 (Stratagene, San Diego, Calif.) were seeded into 25 cm$^2$ tissue culture flasks (at a density of 0.3×10$^6$ cells/ml) and were grown for 3 days in DME medium (Gibco BRL) supplemented with 10% FBS and in the presence or absence of either 10 mg/ml of CoQ10-PTS formulation or the same concentration of vitamin E-PTS formulation, which were added directly to the tissue culture media. The flasks were sealed in an anaerobic chamber containing Gas Pak Plus gas generator envelopes and were incubated in the anaerobic conditions at 37° C. for 17.5 hours in glucose-free medium. Following the hypoxic treatment the cells were placed again in the complete medium (with and without CoQ10 or vitamin E) and were analysed either immediately (time 0) or were cultured for the additional 24 hr under the normoxic conditions. Cell viability was measured by trypan blue exclusion assay. The results are summarized in FIG. 5.

In both experimental paradigms, the CoQ10 and Vitamin E treatments, the percentage of death during the 24 hr recovery period from hypoxia is reduced by half. This demonstrates that the protective effects of CoQ10 against hypoxia-induced cellular damage are comparable to those of vitamin E, the antioxidant with proven efficacy.

Example 20 demonstrates the protective effects of CoQ10 against ischemia/reperfusion caused tissue damage. Although the animal model used is the experimental paradigm of human stroke, the data is relevant for any application where a tissue is damaged as a result of ischemia/reperfusion.

Example 20

Protective Effects of CoQ10 Against Ischemia/Reperfusion

Adult spontaneously hypertensive rats (SHR) weighting 225–250 g, which readily develop stroke characteristic lesions after short periods of vessel occlusion, were used for the middle cerebral artery occlusion model (MCAO). The animals were anaesthetized and the right common carotid artery was permanently occluded. The skull was exposed and the right middle cerebral artery (MCA) was accessed through a 2 mm burr hole in the skull. Under a dissecting microscope a microclip was applied to the MCA vessel. After a 60 min occlusion period, the clip was removed and the wounds were closed. The body temperature was maintained throughout surgery and recovery at 37.5° C. using a rectal thermistor probe connected to a heating lamp. CoQ10 (6 mg/kg) was administered intravenously (neck vein) immediately after the removal of the clip. The effects of 60 min ischemia were quantitated by tetrazolium salt TTC (2,3,5-triphenyl,2H-tetrazolium chloride).

In order to quantitate the tissue damage, the brains were cut into 5 mm coronal sections and were stained overnight with 2% TTC. The coloured formazan was extracted using acetonitrile and its concentration was measured spectrophotometrically at 480 nm. The results as expressed as OD/g of dry brain tissue.

TABLE 12

Protective effects of CoQ$_{10}$ against ischemia-induced brain damage

| | Untreated animals | | | CoQ$_{10}$-treated animals | |
|---|---|---|---|---|---|
| Time after reperfusion | Left brain hemisphere | Right brain hemisphere | Time after reperfusion | Left brain hemisphere | Right brain hemisphere |
| sham | 1250.0 +/−31.8 | 1239.0 +/−11.9 | sham | 1250.0 +/−31.8 | 1239.0 +/−11.9 |
| 1 day | 1208.0 +/−19.2 | 1018.0 +/−26.0 | 1 day | 1206.0 +/−50.2 | 1200.0 +/−19.2 |
| 2 days | 1104.0 +/−36.2 | 898.3 +/−19.6 | 2 days | 1084.9 +/−22.2 | 1060.9 +/−21.2 |

Tetrazolium salts are histochemical indicators of mitochondrial respiratory enzymes and are used to detect tissue infarcts. TTC reacts with intact oxidative enzyme systems, such as succinate and NADH dehydrogenase, accepts electrons and becomes reduced to a colored formazan which stains tissue red. By contrast, irreversible damaged mitochondria that do not have intact oxidative system cannot reduce TTC and the tissue remains white unstained. Accordingly, the healthier the tissue the higher the OD readings. Compare values obtained for brains of sham operated control rats (approximately 1250 OD/g of tissue) and for brains of experimental rats 898.3 OD/g tissue). The protective effects of CoQ10 against ischemia-induced tissue damage are clearly evident, higher TTC content and, hence, the higher OD readings were obtained from brains of animals which received CoQ10-treatment postischemically Example 21 illustrate applicability and suitability of water soluble CoQ10 compositions in cosmetics.

Example 21

Water soluble CoQ10 Compositions in Cosmetics

TABLE 13

| Preparation of cosmetics | | |
|---|---|---|
| CoQ10-PCS-600 100 mg/ml | | Final CoQ10 concentration |
| | Classic Moisturizing Cream Oil of Olay | |
| 1.5 ml | 60 ml | 0.25% |
| 3.0 ml | 60 ml | 0.50% |
| | Classic Moisturizing Cream Oil of Olay | |
| 1.5 ml | 60 ml | 0.25% |
| 3.0 ml | 60 ml | 0.50% |
| | Dry Skin Moisturizer Pond's | |
| 5 ml | 200 ml | 0.25% |
| | Moisturizing Body Lotion Vaseline | |
| 7.5 ml | 300 ml | 0.25% |
| | Moisturizing Body Lotion Oil of Olay | |
| 5 ml | 200 ml | 0.25% |

Table 13 shows amounts of starting materials used to prepare CoQ10-containing skin products which were combined according to the following procedure. The two components were mixed together at room temperature until they formed a uniform composition of a cream in which Coenzyme Q10 remained water soluble. This was tested by adding water to a 0.2 ml sample of cream (total volume of 1 ml). The samples were vigorously vortexed and centrifuged to separate phases. The aqueous phase remained yellow since it contained dissolved CoQ10. The creams were stable and no phase separation was observed even after several months at room temperature.

These cosmetics were tested on 20 healthy volunteers over one year period. All reported improved skin conditions, i.e. improved skin elasticity and reduction of wrinkles. None reported an adverse reaction.

Example 22 illustrates preparation of water soluble compositions containing polyene macrolide antibiotics.

Example 22

Preparation of Compositions of Anti-fungal Antibiotics

TABLE 14

| Preparation of water-soluble formulations of anti-fungal antibiotics | | |
|---|---|---|
| Candicidin | 0.01 | g |
| PCS-600 or PTS-600 | 0.02 | g |
| THF/H$_2$O (8:2, v/v) | 0.1 | ml |
| H$_2$O | 2.5 | ml |
| Nystatin | 0.01 | g |
| PCS-600 or PTS-600 | 0.02 | g |
| Glacial acetic acid | 0.1 | ml |
| H$_2$O | 2.5 | ml |
| Amphotericin B | 0.01 | g |
| PCS-600 or PTS-600 | 0.02 | g |
| Methanol/Glacial acedic acid (2:1, v/v) | 0.3 | ml |
| H$_2$O | 2.5 | ml |

Table 14 shows amounts of starting materials used to prepare water-soluble compositions of antibiotics. Antibiotics and solubilizing agents were dissolved separately in an appropriate solvent or solvent mixture. The solutions were combined and diluted with water. Solvents and excess of water were removed by evaporation under a reduced pressure. When glacial acetic acid was used as solvent, the co-evaporation with water was repeated several times. Compositions containing 20 mg/ml of antibiotic were obtained by solvent evaporation. They were stable and could be stored frozen for extensive periods of time (8 months). These compositions could be also isolated, further concentrated and sterilized by the technique described in Example 11. The final products were waxy, clear pellets which could be best stored frozen, in vials sealed under argon (up to 8 months). They could be reconstituted in aqueous media (water or saline) to desired concentrations.

What is claimed is:

1. A water-soluble composition comprising a bioactive lipophilic compound and a solubilizing agent of the formula

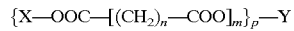

$${X-OOC-[(CH_2)_n-COO]_m}_p-Y$$

wherein: x is a residue of a hydrophobic moiety, selected from the group consisting of sterols, tocopherols, and derivatives thereof, y is a residue of a hydrophilic moiety, selected from the group consisting of polyethers, polyalcohols, and derivatives thereof, p is 1 or 2, m is 0 or 1, and n is an integer in the range $0 \leq n \leq 18$, provided that:

when p and m are equal to 1 and the hydrophobic moiety is cholesterol, n is greater than 4 and not equal to 8, and when p and m are equal to 1, and the hydrophobic moiety is (+)-α-tocopherol, n is not equal to 2.

2. A composition according to claim 1, wherein the bioactive lipophilic compound is selected from the group consisting of ubiquinones, ubiquinols, vitamins, provitamins, polyene macrolide antibiotics, and mixtures thereof.

3. A composition according to claim 1, wherein the hydrophobic moiety is selected from the group consisting of cholesterol, 7-dehydrocholesterol, campesterol, sitosterol, ergosterol, stigmasterol, and α-, β-, γ- , and δ-tocopherols.

4. A composition according to claim 3, wherein the the hydrophilic moiety is a polyether.

5. A composition according to claim 4, wherein the polyether is selected from the group consisting of polyethylene glycols.

6. A composition according to claim 5, wherein the polyethylene glycol has an average molecular weight of from about 300 to about 5000.

7. A composition according to claim 6, wherein the polyethylene glycol has an average molecular weight of from about 600 to about 1000.

8. A composition according to claim 7, wherein the hydrophobic moiety is selected from the group consisting of cholesterol, β-sitosterol, α-(+)-tocopherol and α-(±)-tocopherol, and n is an integer from 2 to 10.

9. A composition according to claim 8, wherein the bioactive lipophilic compound is selected from the group consisting of ubiquinones, ubiquinols, sterols, vitamin E, vitamin A, provitamin A, vitamin K, vitamin D, amphotericin-B, nystatin, candicidin, and mixtures thereof.

10. A composition according to claim 9, wherein the ubiquinione and ubiquinol are of the formula

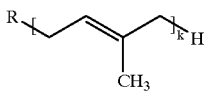

wherein R is

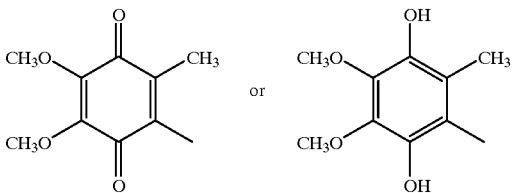

and k is an integer of from 6 to 12.

11. A composition according to claim 10, wherein k is equal to 10.

12. A composition according to claim 9, further comprising a pharmaceutically acceptable, water-soluble additive.

13. A composition according to claim 12, wherein the additive is selected from the group consisting of vitamin C, gelatin, a protein supplement, a polyethylene glycol having a molecular weight greater than about 5000, and mixtures thereof.

14. A method of preparing a water-soluble composition according to claim 1, which method comprises the steps of:
preparing a mixture of the lipophilic compound and the solubilizing agent in a predetermined molar ratio, and
heating the mixture at a temperature higher than the respective melting points of the lipophilic compound and the solubilizing agent, for a time necessary to obtain a clear melt, and
recovering the water-soluble composition so obtained.

15. A method according to claim 14, wherein the molar ratio of the bioactive lipophilic compound and the solubilizing agent is from about 1:1 to about 1:5.

16. A method according to claim 15, wherein the molar ratio is about 1:2.

17. A method of preparing a water-soluble composition according to claim 1, which method comprises the steps of:
dissolving the bioactive lipophilic compound and the solubilizing agent in a predetermined molar ratio in a water-miscible organic solvent,
diluting the solution with a predetermined amount of water, and
removing from the solution the organic solvent and optionally an amount of water necessary to achieve a desired concentration of the water-soluble composition.

18. A method according to claim 17, wherein the organic solvent and water are removed by evaporation under reduced pressure.

19. A method according to claim 18, wherein the molar ratio of the bioactive lipophilic compound and the solubilizing agent is from about 1:1 to about 1:5.

20. A method according to claim 19, wherein the molar ratio is about 1:2.

21. A method of purifying a water-soluble composition according to claim 1, which method comprises the steps of:
dissolving the water-soluble composition in water, at a ratio of the composition to water not exceeding 1:2 by volume,
heating the solution for a time necessary to achieve separation of the water-soluble composition as a liquid phase, and
separating the liquid phase from the hot solution, while keeping the temperature of the solution substantially unchanged.

22. A method according to claim 21, wherein the separation of the liquid phase from the solution is achieved by centrifugation.

23. A pharmaceutical or cosmetic formulation comprising a pharmaceutically or cosmetically effective amount of a bioactive lipophilic compound in the form of a water-soluble composition according to claim 1, said formulation further comprising a pharmaceutically or cosmetically acceptable additive or vehicle selected from the group consisting of solvents, adjuvants, sweeteners, fillers, colourants, flavouring agents, lubricants, binders, moisturizing agents, preservatives and mixtures thereof.

24. A formulation according to claim 23, wherein the bioactive lipophilic compound is selected from the group consisting of ubiquinones, ubiquinols, vitamins, provitamins, polyene macrolide antibiotics, and mixtures thereof.

25. A formulation according to claim 23, wherein the hydrophobic moiety is selected from the group consisting of cholesterol, 7-dehydrocholesterol, campesterol, sitosterol, ergosterol, stigmasterol, and α-, β, γ-, and δ-tocopherols.

26. A formulation according to claim 25, wherein the the hydrophilic moiety is a polyether.

27. A formulation according to claim 26, wherein the polyether is selected from the group consisting of polyethylene glycols.

28. A formulation according to claim 27, wherein the polyethylene glycol has an average molecular weight of from about 300 to about 5000.

29. A formulation according to claim 28, wherein the polyethylene glycol has an average molecular weight of from about 600 to about 1000.

30. A formulation according to claim 29, wherein the hydrophobic moiety is selected from the group consisting of cholesterol, β-sitosterol, α-(+)-tocopherol, and α-(±)-tocopherol, and n is an integer from 2 to 18.

31. A formulation according to claim 30, wherein the bioactive lipophilic compound is selected from the group consisting of ubiquinones, ubiquinols, sterols, vitamin E, vitamin A, provitamin A, vitamin K, vitamin D, amphotericin-B, nystatin, candicidin, and mixtures thereof.

32. A formulation according to claim 31, wherein the ubiquinione and ubiquinol are of the formula

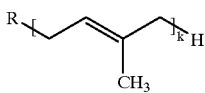

wherein R is

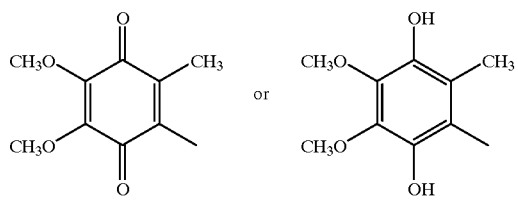

and k is an integer of from 6 to 12.

33. A formulation according to claim 32, wherein k is equal to 10.

34. A formulation according to claim 23, in a form suitable for topical, oral, or parenteral administration.

35. A formulation according to claim 34, in the form of a capsule, tablet, caplet, granulate, suppository, sterile solution, cream, lotion, gel, or ointment.

36. A method of the prophylaxis or treatment of a medical disorder associated with oxidative tissue damages or mitochondrial dysfunctions, which method comprises administering to a human or a warm-blooded animal in need of such prophylaxis or treatment a therapeutically effective amount of a water-soluble composition according to claim 1 comprising Coenzyme $Q_{10}$ as the bioactive lipophilic compound, in conjunction with a pharmaceutically acceptable diluent or carrier.

37. A method according to claim 36, wherein the disorder is selected from the group consisting of heart diseases, ischemia/reperfusion tissue damages, neurodegenerative disorders and mitochondrial encephalomyolopaties.

38. A method of the prophylaxis or treatment of a medical disorder requiring Coenzyme $Q_{10}$ as an adjuvant, which method comprises administering to a human or a warm-blooded animal in need of such prophylaxis or treatment a therapeutically effective amount of a water-soluble composition according to claim 1 comprising Coenzyme $Q_{10}$ as a bioactive lipophilic compound, in conjunction with a pharmaceutically acceptable diluent or carrier.

39. A method according to claim 38, wherein the disorder is selected from the group consisting of hypercholesteremia, infectious diseases and cancers.

40. A method of the treatment of a fungal infection, which method comprises administering to a human or a warm-blooded animal in need of such treatment a therapeutically effective amount of a water-soluble composition according to claim 1 comprising a macrolide polyene antibiotic as the bioactive lipophilic compound, in conjunction with a pharmaceutically acceptable diluent or carrier.

41. A method of preparing a water-soluble composition of Coenzyme $Q_{10}$, which method comprises the steps of directly dissolving a non-crystallized product of synthesis of Coenzyme Q10 in a solubilizing agent of the formula

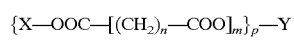

wherein: x is a residue of a hydrophobic moiety, selected from the group consisting of sterols, tocopherols, and derivatives thereof, y is a residue of a hydrophilic moiety, selected from the group consisting of polyethers, polyalcohols, and derivatives thereof, p is 1 or 2, m is 0 or 1, and n is an integer in the range $0 \leq n \leq 18$, provided that:

when p and m are equal to 1 and the hydrophobic moiety is cholesterol, n is greater than 4 and not equal to 8, and when p and m are equal to 1, and the hydrophobic moiety is (+)-α-tocopherol, n is not equal to 2, and recovering the water-soluble composition so obtained.

42. A method according to claim 41, further comprising a purification of the water-soluble composition, said purification comprising the steps of:

dissolving the water-soluble composition in water, at a ratio of the composition to water not exceeding 1:2 by volume, heating the solution for a time necessary to achieve separation of the water-soluble composition as a liquid phase, and separating the liquid phase from the hot solution, while keeping the temperature of the solution substantially unchanged.

43. A method according to claim 42, wherein the separation of the liquid phase from the solution is achieved by centrifugation.

44. A composition according to claim 4, wherein the molar ratio of the bioactive lipophilic compound and the solubilizing agent is from about 1:1 to about 1:5.

45. A composition according to claim 7, wherein the molar ratio of the bioactive lipophilic compound and the solubilizing agent is about 1:2.

* * * * *